(12) United States Patent
Koplin et al.

(10) Patent No.: US 11,640,858 B2
(45) Date of Patent: *May 2, 2023

(54) DIGITAL THERAPEUTIC PLATFORM

(71) Applicant: EYETHENA CORPORATION, New York, NY (US)

(72) Inventors: Richard S. Koplin, New York, NY (US); Geoff Scott, New York, NY (US)

(73) Assignee: EYETHENA CORPORATION, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,511

(22) Filed: Oct. 5, 2022

(65) Prior Publication Data

US 2023/0022047 A1 Jan. 26, 2023

Related U.S. Application Data

(63) Continuation of application No. 17/668,362, filed on Feb. 9, 2022, now Pat. No. 11,468,993.

(Continued)

(51) Int. Cl.
*G16H 50/20* (2018.01)
*G06N 7/00* (2023.01)
(Continued)

(52) U.S. Cl.
CPC .............. *G16H 50/20* (2018.01); *G06N 7/005* (2013.01); *G16H 10/60* (2018.01); *G16H 40/67* (2018.01)

(58) Field of Classification Search
CPC ........ G16H 50/20; G16H 40/67; G16H 10/60; G06N 7/005
See application file for complete search history.

(56) References Cited

U.S. PATENT DOCUMENTS

2006/0010090 A1* 1/2006 Brockway ............ A61B 5/7264
600/300
2007/0118399 A1* 5/2007 Avinash ................. G16H 40/20
705/2

(Continued)

FOREIGN PATENT DOCUMENTS

KR 10-2021-0009683 A 1/2021

OTHER PUBLICATIONS

An International Search Report and Written Opinion of the International Searching Authority dated Jun. 7, 2022 in connection with International application No. PCT/US2022/015877.

(Continued)

*Primary Examiner* — Mark Holcomb
(74) *Attorney, Agent, or Firm* — Baker & McKenzie

(57) ABSTRACT

Systems and methods are provided for monitoring health. An exemplary method includes: collecting a first data regarding a patient during an in-office visit; providing a remote monitoring service for remotely monitoring the patient's health; remotely collecting, using the remote monitoring service, a second data of the patient; providing a probabilistic network for assigning metric-based information to the plurality of data using a plurality of conditional probabilities; processing, using the probabilistic network, the first data and the second data using the probabilistic network; generating, using the processed plurality of data, one or more machine learning models for producing a knowledge base trained to recognize pattern types in the data; generating, using the knowledge base, one or more artificial intelligent features for recommending treatment options based on the data regarding the patient; and providing, using the one or more artificial intelligent features, one or more treatment recommendations for improving the patient's health.

20 Claims, 7 Drawing Sheets

Related U.S. Application Data

(60) Provisional application No. 63/148,075, filed on Feb. 10, 2021.

(51) Int. Cl.
*G16H 10/60* (2018.01)
*G16H 40/67* (2018.01)

(56) References Cited

U.S. PATENT DOCUMENTS

| | | |
|---|---|---|
| 2019/0034589 A1 | 1/2019 | Chen et al. |
| 2019/0057774 A1* | 2/2019 | Velez .................... G06N 20/00 |
| 2019/0110753 A1 | 4/2019 | Zhang et al. |
| 2019/0189253 A1 | 6/2019 | Kartoun et al. |
| 2019/0209022 A1* | 7/2019 | Sobol .................... A61B 5/0022 |
| 2021/0007643 A1 | 1/2021 | Lamrani et al. |
| 2021/0313049 A1* | 10/2021 | Khan .................... G16H 50/70 |

OTHER PUBLICATIONS

Koplin, Richard S. et al., "Clinical Overview Supporting the Eyethena™ Product: Glaucoma Prescription Digital Therapeutics™," Company Snapshot, Sep. 6, 2021.

Eyethena Corporation, "Improving outcomes for glaucoma with continual patient monitoring and support," Company Overview, Sep. 2021.

\* cited by examiner

DIGITAL THERAPEUTIC PLATFORM

CROSS REFERENCE TO RELATED APPLICATIONS

This application is a continuation of U.S. patent application Ser. No. 17/668,362 filed on Feb. 9, 2022, which claims priority to U.S. Provisional Application No. 63/148,075 filed on Feb. 10, 2021, the disclosures of which are hereby incorporated by reference in their entirety.

BACKGROUND

Eye ailments, like glaucoma, may encompass a panoply of disorders of the eye often related to elevated eye pressure, but occasionally not (low tension glaucoma), that when poorly controlled (or left untreated) may cause damage to the optic nerve and its vascular infrastructure. The results of progressive damage to the optic nerve is initially loss of the peripheral field of vision and ultimately central vision.

The elements of many eye ailment diagnoses are often serendipitous. Since many early pathological consequences of eye ailments are asymptomatic in nature, patients may only discover they have a problem during a routine eye exam, perhaps when they visit an optometrist or ophthalmologist for a change in glasses.

A diagnosis of certain eye ailments may usually imply a chronic disorder requiring continued (lifetime) evaluations and may include a variety of treatment measures often involving multiple topical medications and occasionally various laser and invasive surgical procedures.

Glaucoma is not a curable disease in the routine sense and therefore patients often harbor significant negative cognitive overlay towards the threat the disease represents—including blindness. Often, these disruptive cognitive concerns, counterintuitively, inhibit a patient's therapeutic compliance and may delay visits to their practitioners resulting in progression of their disease. Likewise, the cognitive disruption suffered by the patient may be an impediment to a fuller understanding of the disease. The diagnosis of eye ailments may inflict a life-long psychological burden. Only recently have studies begun to describe the psychometric process associated with eye ailments, such as glaucoma.

Coincidentally, ongoing research is also exploring whether physiological changes seen in depression may play a role in increasing the risk of physical illness. NIH studies describe patients with chronic depression as being more likely to develop significant co-morbidities. These may include one or more of the following: signs of increased inflammation, changes in the control of heart rate and blood circulation, abnormalities in stress hormones, or metabolic changes typical of those seen in people at risk for diabetes.

BRIEF SUMMARY

According to one aspect of the subject matter described in this disclosure, a method for monitoring health is provided. The method includes the following: collecting, using at least one processor, a plurality of data regarding a patient; providing, using the at least one processor, a probabilistic network for assigning metric-based information to the plurality of data using a plurality of conditional probabilities; processing, using the at least one processor, the plurality of data using the probabilistic network; generating, using the at least one processor and the processed plurality of data, one or more machine learning models for producing a knowledge base trained to recognize pattern types in the data; generating, using the at least one processor and the knowledge base, one or more artificial intelligent features for recommending treatment options based on the data regarding the patient; and providing, using the at least one processor and the one or more artificial intelligent features, one or more treatment recommendations for improving the patient's health.

According to another aspect of the subject matter described in this disclosure, a method for monitoring health is provided. The method includes the following: collecting, using at least one processor, a first data regarding a patient during an in-office visit; providing, using the at least one processor, a remote monitoring service for remotely monitoring the patient's health; remotely collecting, using the remote monitoring service and the at least one processor, a second data of the patient; providing, using the at least one processor, a probabilistic network for assigning metric-based information to the first data and the second data using a plurality of conditional probabilities; processing, using the at least one processor and the probabilistic network, the first data and the second data using the probabilistic network; generating, using the at least one processor and the processed plurality of data, one or more machine learning models for producing a knowledge base trained to recognize pattern types in the data; generating, using the at least one processor and the knowledge base, one or more artificial intelligent features for recommending treatment options based on the data regarding the patient; and providing, using the at least one processor and the one or more artificial intelligent features, one or more treatment recommendations for improving the patient's health.

According to another aspect of the subject matter described in this disclosure, a system for monitoring health is provided. The system includes one or more computing device processors. One or more computing device memories are coupled to the one or more computing device processors. The one or more computing device memories store instructions executed by the one or more computing device processors, wherein the instructions are configured to: collect a first data regarding a patient during an in-office visit; provide a remote monitoring service for remotely monitoring the patient's health; remotely collect, using the remote monitoring service, a second data of the patient; provide a probabilistic network for assigning metric-based information to the first data and the second data using a plurality of conditional probabilities; process the first data and the second data using the probabilistic network; generate, using the processed plurality of data, one or more machine learning models for producing a knowledge base trained to recognize pattern types in the data; generate, using the knowledge base, one or more artificial intelligent features for recommending treatment options based on the data regarding the patient; and provide, using the one or more artificial intelligent features, one or more treatment recommendations for improving the patient's health.

Additional features and advantages of the present disclosure are described in, and will be apparent from, the detailed description of this disclosure.

BRIEF DESCRIPTION OF THE DRAWINGS

The disclosure is illustrated by way of example, and not by way of limitation, in the figures of the accompanying drawings in which like reference numerals are used to refer to similar elements. It is emphasized that various features

DETAILED DESCRIPTION

Figure 1:
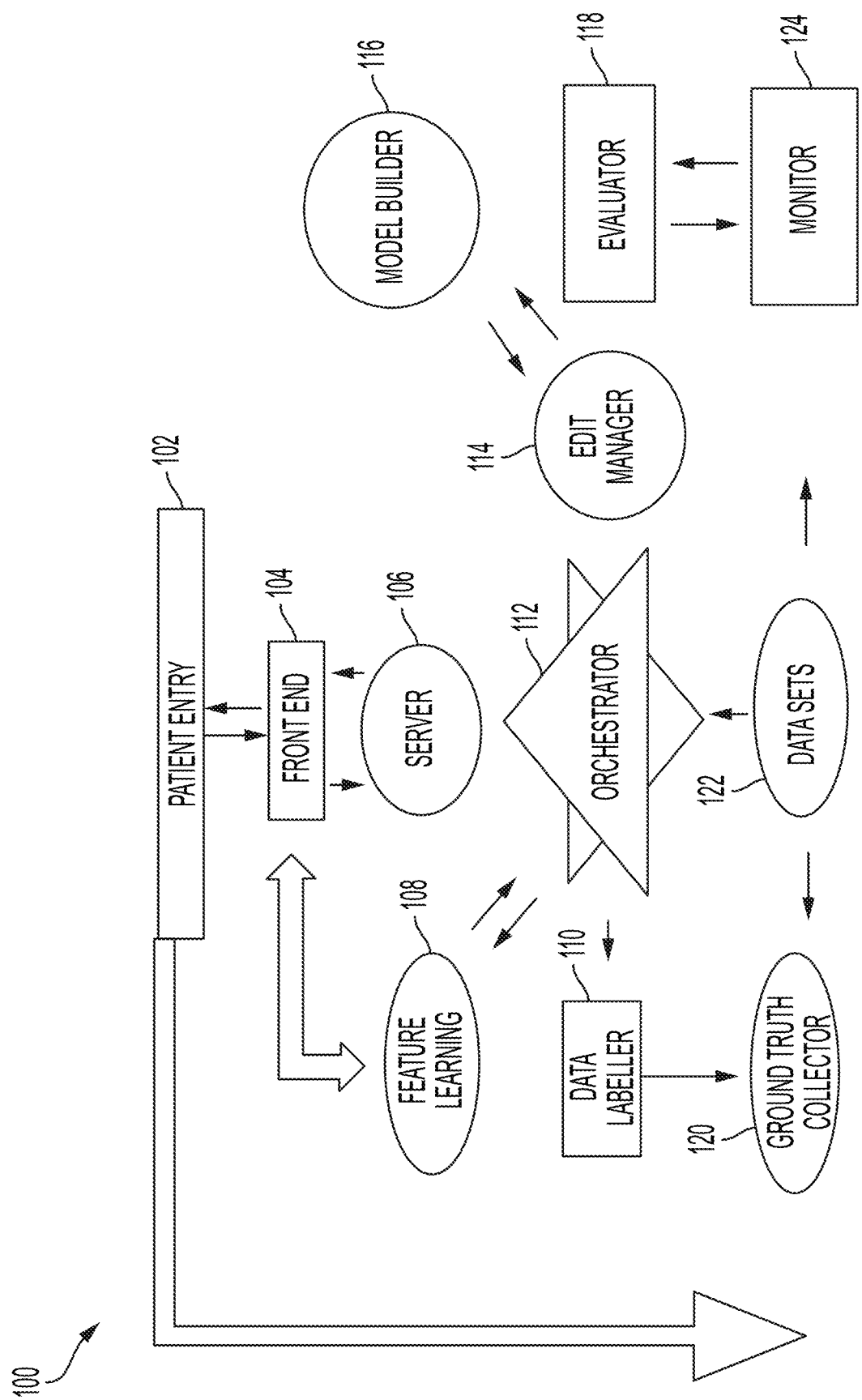
FIG. 1 is a schematic diagram of the machine learning (ML) architecture for a digital medical platform, in accordance with some embodiments.

The figures and descriptions provided herein may have been simplified to illustrate aspects that are relevant for a clear understanding of the herein described devices, systems, and methods, while eliminating, for the purpose of clarity, other aspects that may be found in typical similar devices, systems, and methods. Those of ordinary skill may recognize that other elements and/or operations may be desirable and/or necessary to implement the devices, systems, and methods described herein. But because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

The terminology used herein is for the purpose of describing particular example embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. That is, terms such as "first," "second," and other numerical terms, when used herein, do not imply a sequence or order unless clearly indicated by the context.

This disclosure describes an integrated digital therapeutic platform intended to remotely monitor a patient's mental as well as physical eye health. While the disclosure may reference treatment of eye ailments, the digital therapeutic platform may be applicable to remotely monitoring the health of patients with other health ailments. Input data may be harvested through both direct physician-patient interaction (as in classic office visits) and also through interaction with a remote monitoring service described herein. Identifiable data sets may be made available via the digital therapeutic platform. Therefore, the patient's responsible medical professionals may be provided consistent oversight to the patient's eye health and the need for adjustments to treatments as well as their mental health status in relation to medication and other testing/treatment protocol adherence.

Depending on the data collection, the digital therapeutic platform may use a belief-based network (Bayesian or Bayes) of conditional probabilities assigning sensitivity and specificity of assignable metric based information to data received, such as intraocular pressure (TOP), optic nerve cup/disc ratios, or the like. The weighted probabilities may be combined so that it results in providing one or more specific diagnoses for the patient. Processing the plethora of eye related data in this manner may point towards appropriate treatment options and define more granular diagnostics.

Alternatively, the patient's mental health (behavioral/cognitive status) may be more tuned to heuristic reasoning, which may allow for using a methodology to create a differential diagnosis based on evidence that is only partial in nature.

Using scheduled and unscheduled timely provocations, a patient's interactions with a remote monitoring service may provide a stream of eye specific data sets as well as behavioral specific data sets. HIPPA compliant methodology may be provided. The ongoing data sets may be curated by the machine learning (ML) and artificial intelligence (AI) algorithms and may produce a relevant source of digital driven therapeutic options available for evaluation by the patient's treating physicians. Besides using ML and AI algorithms, the digital therapeutic platform may use heuristic approaches for producing a relevant source of digital driven therapeutic options.

Remote patient monitoring, as an integrative element, may include, as example, historic and remote monitored diagnostic data capture using a remote monitoring service. The diagnostic data may include one or more of the following: computer-generated self-testing of visual fields, visual acuity, including optic nerve photography as well self-testing for IOP. The diagnostic data may also include app usage, educational content usage, medication and testing protocol adherence, responses to provocations, and other indicators of a patient's mental health. These data sets, set in an ML and AI protocol environment, in aggregate, may speak to the stability or instability of a patient's disease state—both psychologically and ophthalmologically.

The digital therapeutic platform may measure cognitive, behavioral, and ophthalmic physical data metrics associated specifically to a patient's eye ailment diagnosis (and vicariously, co-morbid concerns) using a suite of ML and AI algorithms. Through physician direct intervention (prescribed medications, laser and surgical techniques) supported by the digital therapeutic platform, algorithms based on the accumulated experience (ML)—including ophthalmic specific sourced data—in concert with the knowledge imparted by the accumulated data (AI) a treating physician is capable of maintaining an inclusive oversight of the patient's condition both from a cognitive as well as an ophthalmologic perspective. This holistic digital arrangement may auger well for the patient's ability to stabilize the disease, preserve vision, and medication and treatment adherence.

This disclosure contemplates the digital therapeutic platform to use its ML and AI algorithms to aggregate data with increasing patient/physician utilization. The increasing data may provide improved accuracy and stability. The digital therapeutic platform may use a tree decision methodology but may use other methodology/algorithms for its decision making.

The digital therapeutic platform may use as input a defined set of source materials (behavioral or specific ophthalmic data). While harvesting specific eye related disease information, the digital therapeutic platform may maintain the patient's digital therapeutic compliance, and the stress related cognitive overlay associated with the patient's eye ailments, treatment, and long-term implications may be mitigated. The digital therapeutic platform may leverage ML pattern recognition algorithms to produce a knowledge base for its number of Artificial Intelligence (AI) features.

The digital therapeutic platform may use a patient's in-office data that is obtained at a doctor's office to establish the patient's baseline as well as populate needed data for its ML and AI algorithms. The patient's in-office data may include one or more of the following: visual acuity (BCVA), visual field evaluation, optic nerve assessment: direct visualization of nerve/optic disc photography, optical coherence tomography of the optic disc and macula, intraocular pressure (TOP), gonioscopic data, ultrasonic biomicroscopy findings, corneal pachymetry, axial length, color vision, to illuminate risk factors. The optic nerve assessment may include direct visualization of the nerve/optic disc photography to detect cupping, color, rim defects, presence or absence of disc hemorrhage, or the like. The risk factors may include one or more of the following: age, family history of glaucoma (or other ocular comorbidities), refractive error, central corneal thickness (as measured by ultrasound pachymetry), pattern standard deviation on visual field, vertical cup-to-disc ratio, TOP, character of the anterior chamber, its angle, rheumatoid disease, ocular inflammatory disorders, race, and others not enumerated. Each of these may be given a numeric risk factor to be considered by the ML and AI algorithms described herein.

The mental health component of the digital therapeutic platform may rely on evaluation of cognitive processes that may be involved with ongoing patient interrogatories, app usage, educational content usage, and medication and testing protocol adherence. The digital therapeutic platform may give a practitioner an opportunity to track negative behavioral and cognitive issues that may interfere with a patient's eye treatment; importantly adherence to treatment regimens (eye drops in particular). The digital therapeutic platform may include ML algorithms based on behavioral and cognitive archetypes to provide relevant "knowledge" that is then capable of being processed through the AI algorithms. The digital therapeutic platform therefore may provide graded cognitive therapeutic prescriptive sets that are responsive to the patient's unique needs.

FIG. 1 is a schematic diagram of the ML architecture for a digital therapeutic platform 100. The digital therapeutic platform may include a front end 104 receiving patient entry 102 associated with information of a patient from either a user or an automated system. The front end 104 may process patient entry 102 directly and send the results to server 106. Server 106 may receive requests from front end 104 associated with processing patient entry 102 or performing analysis using the ML architecture. Server 106 may return the results of the requests it processed to front end 104.

In some implementations, the patient entry 102 may not be processed by front end 104 and may directly be sent to server 106 for processing. In some embodiments, the front end 104 may be a browser or web-based mobile application. In some embodiments, server 106 may be a cloud computing system or a data server.

When the raw data associated with patient entry 102 is provided to front end 104, the front end 104 may utilize Feature Learning component 108. The Feature Learning component 108 may allow digital therapeutic platform 100 to make data pattern discoveries for raw data classification automatically. For example, if a patient's IOP (eye pressure) pattern is persistently "elevated" and associated data suggests loss of visual field, then "discovery" would suggest a pathological process. Here a Bayesian assisted process (as in the "ground truth" classification) is unnecessary since the feature determinants are unsupervised and data input is unlabeled.

A data labeler 110 may be provided for labeling the raw data being received by front end 104. An Orchestrator 112 may allow for an orchestrated data management process, used by server 106, which accelerates testing, retraining, and redeployment of predictive analytics models where the shelf life (interrupted by ongoing data drag) is therefore short. The Orchestrator 112 may manage data being used by Feature Learning component 108, data labeler 110, and data sets 122 used for modeling.

The Model Builder 116 may be a discrete file (or group of files) that has been "trained" to recognize data patterns related to defined pathologies using data sets 122. The data points used by Model Builder 116 may not be absolute since they may be modified by other data patterns processed by the Model Builder 116. An edit manager 114 may allow data points used by Model Builder 116 to be adjusted based on different data patterns. The Model Builder 116 may share with edit manager 114 any changes in the data patterns. The digital therapeutic platform 100 may use the recognized data patterns produced by Model Builder 116 to form models relied on by the ML architecture of digital therapeutic platform 100. Pattern recognition becomes "smart" as the elemental diagnostic data are aggregated.

A Ground truth collector 120 may be provided to determine the accuracy of the data sets 122 used as training data sets having specified classifications for supervised learning. Also, the Ground truth collector 120 may be used in statistical models by Model Builder 116 to provide or disprove research hypotheses. Commonly Bayesian spam filtering (problematic graphical model representing a set of variables) is an example of supervised learning. The filters differ in the case of unsupervised learning techniques, where the model needs no supervision. Supervised learning allows one to collect data or produce data from a previous experience. Unsupervised machine learning may help in discovering many elements of unknown data patterns.

An evaluator 118 may be used to evaluate the models produced by the Model Builder 116 to determine if any updates to the underlying data sets 122 may be needed. The evaluator 118 may determine if updating data sets 122 is required, or other techniques may be needed to improve the models produced by Model Builder 116. The evaluator 118 may use a monitor 124 that continuously monitors if the outputs of the models are outside an acceptable range. Once it is determined the output of a model is outside the acceptable range, monitor 124 may have that model further evaluated by evaluator 118. Over time, it is typical that the accuracy of prediction of a model is lowered and requires updating.

The data produced by the ML architecture may provide the knowledge base required to produce one or more AI features. The ML models produced by model builder 116 may include data files that have been trained to recognize defined data pattern types, which is later used by the one or more AI features to provide treatment recommendations based on the data sets 122 and the models provided.

The digital therapeutic platform 100 may include a technique or methodology to determine a patient baseline. This may include capturing a patient's medical history, as in the case of patient entry 102. The medical history may include information such as Age, family history of glaucoma, race & ethnicity, known medication allergies/adverse reactions, complaints about vision, or overall health. Conventional paper patient questionnaire may be used to a capture patient medical history. In some implementations, the information in the conventional paper patient questionnaire may be entered into as an electronic medical record (EMR) and sent to digital therapeutic platform 100 via integration. In some embodiments, the information in the conventional paper patient questionnaire may be entered directly into digital therapeutic platform 100 via a web interface, such as front end 104. A patient may directly enter into digital therapeutic platform 100 their medical history. In some embodiments, the user may use a mobile app survey or web interface survey to enter such medical history.

The digital therapeutic platform 100 may require information associated with initial clinical observations at a doctor's office involving visual field measurements, optic nerve measurements, IOP measurements, or OCT scans. The visual field measurements may include blind spot enlarged, focal defect, Bjerrum scotoma, arcuate scotoma, or the like. The optic nerve measurements may include cup/disc Ratio (C/D) or observations, such as blood vessel nasalization, thinning temporal rim, or coloration. The IOP measurements may include a numeric value that is normally below 20. Optic nerve damage may occur at well below 20 IOP. Each individual may have their own normal IOP, so IOP alone is not diagnostic for glaucoma or other eye ailments.

The patient may receive a home kit having at-home testing devices. The at-home testing devices may be used to measure IOP, visual field, or optic nerve imaging. In addition, the at-home devices may perform OCT scanning as well. The home kit may include smart-dispensers for measuring eye drop use and sending to digital therapeutic platform 100 medication adherence information. In addition, the home kit may include training materials for connecting the at-home testing devices to the remote monitoring service and administering the at-home tests.

The digital therapeutic platform 100 may require information associated with measured diurnal IOP process at home. In this case, the patient may be assigned a schedule to take IOP measurements at prescribed times of the day over several days (e.g. on waking up, midday, at bedtime, for 3 consecutive days). The patient may receive app notifications at prescribed times to take an IOP measurement. As the patient takes an IOP measurement, the test result data may be sent to digital therapeutic platform via the remote monitoring service using integration (e.g. Bluetooth, API, or the like).

The digital therapeutic platform 100 may calculate the baseline TOP. In particular, the digital therapeutic platform 100 may normalize in-office and at-home TOP measurements. Statistical processes may be used by digital therapeutic platform 100 that takes into account differences in sensitivity of in-office and at-home testing equipment, as well as differences in user skill at administering tests, and the time of day when the measurements were taken. In-office TOP tests may require physically touching the eye with a device, which requires applying a topical anesthetic to the eye, all of which must be performed by trained medical professionals. Also, the digital therapeutic platform 100 may assess visual field and optic nerve condition information that was previously collected. The digital therapeutic platform 100 may define a process to calculate baseline TOP once all measurements have been received.

In some embodiments, the patient may receive notifications from digital platform 100 containing reminders to take their medications according to the dosing schedule prescribed by their doctor. In some embodiments, smart-dispensers may automatically record the dosing of medications. In some embodiments, the patient may be able to manually indicate that they took their prescribed medications.

The digital therapeutic platform 100 may include a technique or methodology to track a patient's overall condition by sending notifications to a patient using prompts/questions designed to inform of the patient's overall condition. The notification may be directed to assess changes to the patient's vision (e.g. blurriness, or the like), changes to their eye condition (e.g. pain, swelling, discharge, redness, itchiness, or the like), mental health status, changes to their overall health, or changes to medications not previously prescribed, or the like.

The digital therapeutic platform 100 may include a technique or methodology to detect disease progression by using at-home clinical observations. In this case, the patient may be assigned a schedule to take routine, self-administered tests, which could include: TOP, visual field, optic nerve imaging, or OCT scan (when available). The digital therapeutic platform 100 may normalize clinical observations so that they can be compared against the baseline. A determination may be made if results are anomalous using one or more statistical or ML techniques. In some embodiments, the ML techniques may include an unsupervised learning approach (anomaly/outlier detection) using one or more of the following: K-means clustering, hierarchical clustering, DBScan clustering, isolation forest, random cut forest, or the like. When routine testing returns anomalous results, the digital therapeutic platform 100 may adjust testing to help determine cause (e.g. perform the same test on waking up, in the middle of the day, and before going to bed for the next 3 days). This may include supporting a set of one or more alternate testing schedules to augment the routine schedule or using simple rules to determine which alternate testing schedule to assign.

The digital therapeutic platform 100 may include a technique or methodology to recommend changes to a treatment protocol. In this case, a doctor may receive a summary of the patient condition including one or more of the following: medication protocol adherence, at-home testing adherence, in-office and telehealth appointment adherence, or mental health status. The doctor may receive notifications for one or more of the following regarding important changes to the patient condition: changes to their vision (e.g. blurriness or the like), changes to their eye condition (e.g. pain, swelling, discharge, redness, itchiness, or the like), changes to their overall health, or changes to medications not prescribed by their doctor. Also, the doctor may receive one or more recommendations from digital therapeutic platform 100 regarding changes to the treatment protocol. The digital therapeutic platform 100 may map a vector of patient information to treatment protocols (e.g. medications, surgical procedures).

The vector of patient information may include one or more of the following: clinical observations (in-office and at-home), mental health status, medical history, medication protocol adherence, at-home testing adherence, in-office and telehealth appointment adherence, engagement with content, utilization of resources, responses to questions designed to inform overall patient condition, or other biometric information. The digital therapeutic platform 100 may classify the vector of patient information using one or more of the following approaches: random decision forest, linear classifier, support vector machine, recurrent neural network, feedforward neural network, radial basis function network, self-organizing map, learning vector quantization, Hopfield network, Boltzmann machine, echo state network, long short term memory, bi-directional recurrent neural network, hierarchical recurrent neural network, stochastic neural network, modular neural network, associative neural network, deep neural network, deep belief network, convolutional neural network, convolutional deep belief network, large memory storage and retrieval neural network, deep Boltzmann machine, deep stacking network, tensor deep stacking network, spike and slab restricted Boltzmann machine, compound hierarchical-deep model, deep coding network, multilayer kernel machine, or deep Q-network.

The classes may be surgical procedures or combinations of medications, of which there are a small number (e.g. <10), and dosing protocols (e.g. 1 drop, 3 times daily on waking up, midday, bedtime). Surgical procedures, medications, and dosing protocols may be different for each eye. If one does not have a recommendation with high-enough probability, the doctor may schedule an in-office or telehealth appointment. The digital therapeutic platform 100 may present ranked recommendations to the doctor, and any custom treatment protocols that the doctor may have configured. The doctor may select one or more changes to the treatment protocol to send to the patient based on the presented recommendations. The doctor recommendations may be reviewed by medical experts, thus expanding the labeled data set. Note that the patient may receive notification based on the doctor selection.

The digital therapeutic platform 100 may include a technique or methodology to recommend educational content and resources to improve testing and medication adherence. Personalized recommendations for educational content and resources to improve testing and medication adherence may be generated based on a patient's diagnosed disease progression and medication adherence. A vector of patient information may be generated by mapping patient information to educational content and resources. In this case, the vector of patient information may include one or more of the following: clinical observations (in-office and at-home), mental health status, medical history, medication protocol adherence, at-home testing adherence, in-office and telehealth appointment adherence, engagement with content, utilization of resources, or responses to questions designed to inform overall patient condition. The vector of patient information may be classified using one or more of the following: random decision forest, linear classifier, support vector machine, recurrent neural network, feedforward neural network, radial basis function network, self-organizing map, learning vector quantization, Hopfield network, Boltzmann machine, echo state network, long short term memory, bi-directional recurrent neural network, hierarchical recurrent neural network, stochastic neural network, modular neural network, associative neural network, deep neural network, deep belief network, convolutional neural network, convolutional deep belief network, large memory storage and retrieval neural network, deep Boltzmann machine, deep stacking network, tensor deep stacking network, spike and slab restricted Boltzmann machine, compound hierarchical-deep model, deep coding network, multilayer kernel machine, or deep Q-network. The classes may include articles, podcasts, videos, communities, support groups, therapists, low-vision coaches, or any other forms of content or resources that may be helpful to patients in various situations. Using the classes and vector of patient information, the digital therapeutic platform 100 may generate a number of recommendations to the patient for consideration. The recommendations may be ranked.

The patient may select content and resources either from the recommendations or from browsing/searching on their own. The digital therapeutic platform 100 may collect data on patient engagement with content and resources (e.g. clicks, scrolling, time on content, interaction with audio/video, etc.) as an indication of relevance to a patient as represented by their vector of patient information at that time.

Figure 2A:
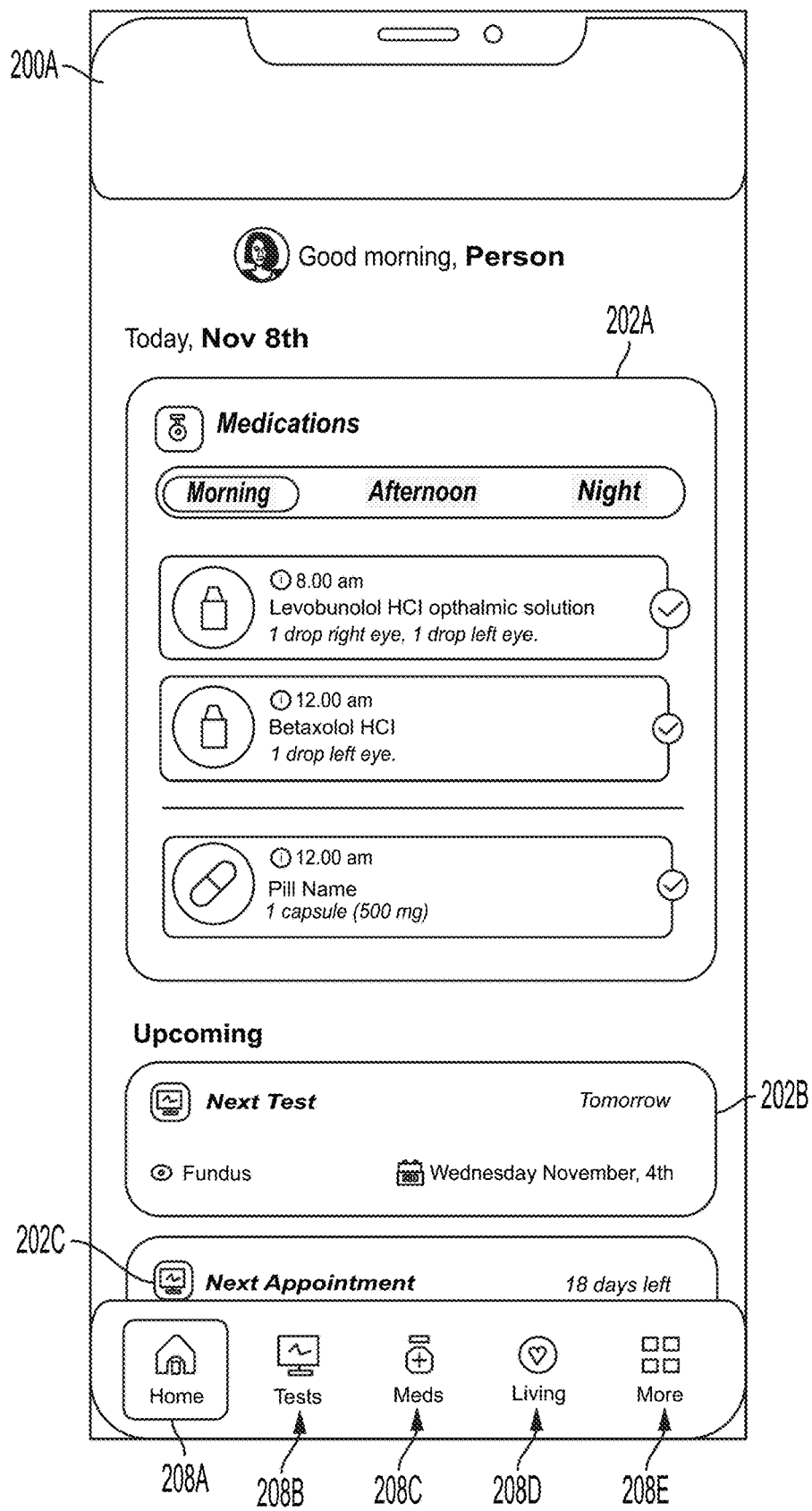
FIGS. 2A-2D are schematic diagrams of example interfaces of the remote monitoring service, in accordance with some embodiments.

FIGS. 2A-2D are schematic diagrams of example interfaces of the remote monitoring service, in accordance with some embodiments. FIG. 2A is a schematic diagram of an example interface 200A of the remote monitoring service. The example interface 200A may include interface elements 202A, 202B, and 202C. The interface element 202A may display reminders of medications to be administered at various times during the current day as prescribed by a patient's doctor, which the remote monitoring service may be actively monitoring. The interface element 202B may display one or more upcoming scheduled tests the patient may need to perform. The results of the upcoming one or more scheduled tests may be monitored by the remote monitoring service and uploaded to the digital therapeutic platform 100 for processing. The interface element 202C may display the patient's next upcoming appointments. The remote monitoring service may track the patient's administration of medications, at-home testing, and in-office appointment history to assess if the patient is adhering to their treatment.

The example interface 200A may include interface elements 208A-208E. The interface element 208A may direct the patient to a home screen, which is indicative of example interface 200A. The interface element 208B may direct the patient to a test page detailing the results of recent tests. The interface element 208C may direct the patient to a medication page detailing a listing of the patient's medications and their compliance. The interface element 208D may direct the patient to a living page detailing a listing of videos and reading materials to assist the patient in understanding their treatment. The interface element 208E may direct the patient to a page detailing contact information, support services, a procedure diary, appointments, or the like.

Figure 2B:
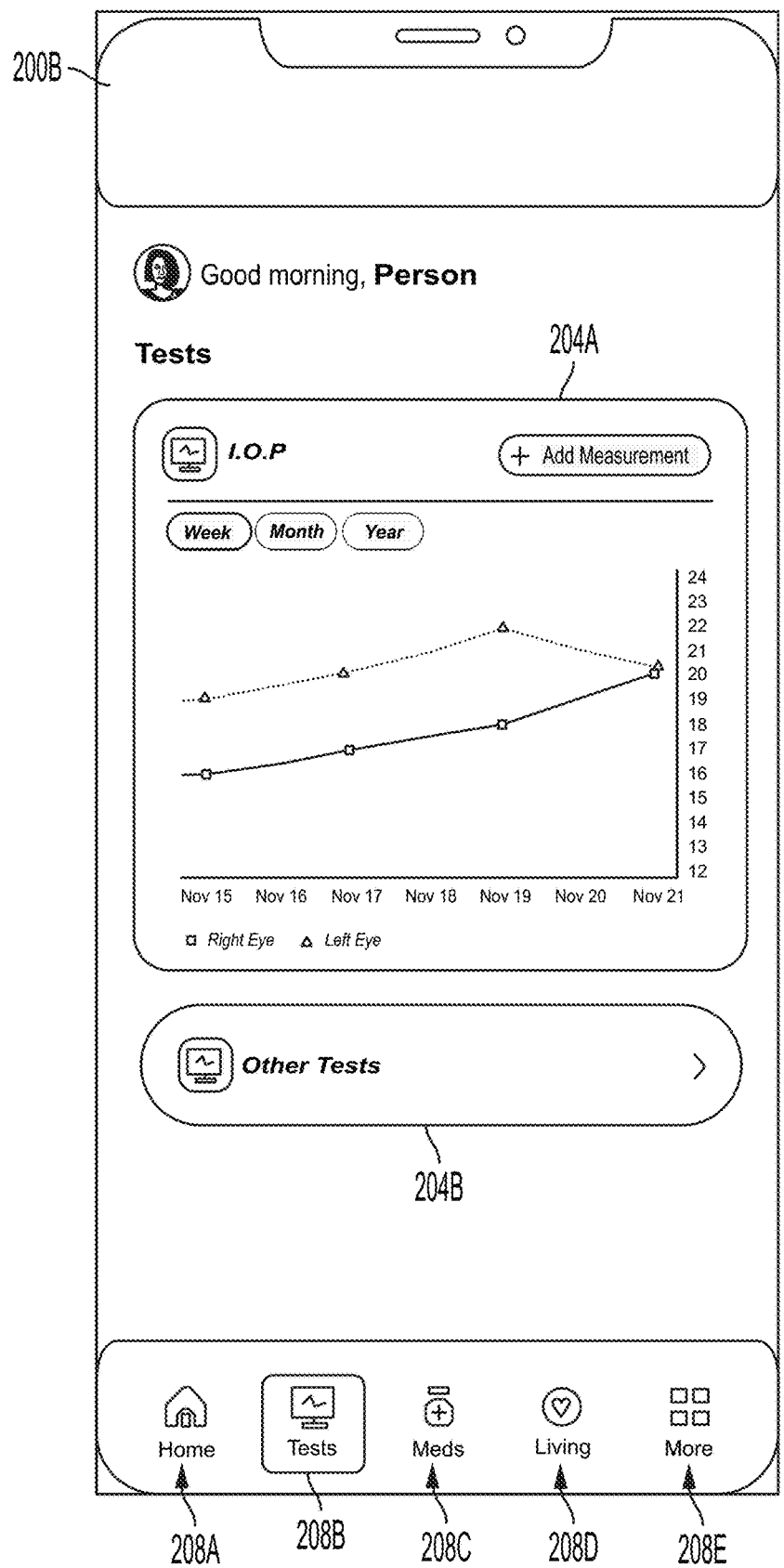

FIG. 2B is a schematic diagram of example interface 200B indicative of the test page of interface element 208B. The example interface 200B may include interface elements 204A-204B. The interface element 204A may display the results of a recent test taken by the patient. In this case, the interface element 204A displays a recent TOP test result taken by the patient remotely. The interface element 204B may display the results of other tests taken by the patient, such as an OCT scan or the like.

Figure 2C:
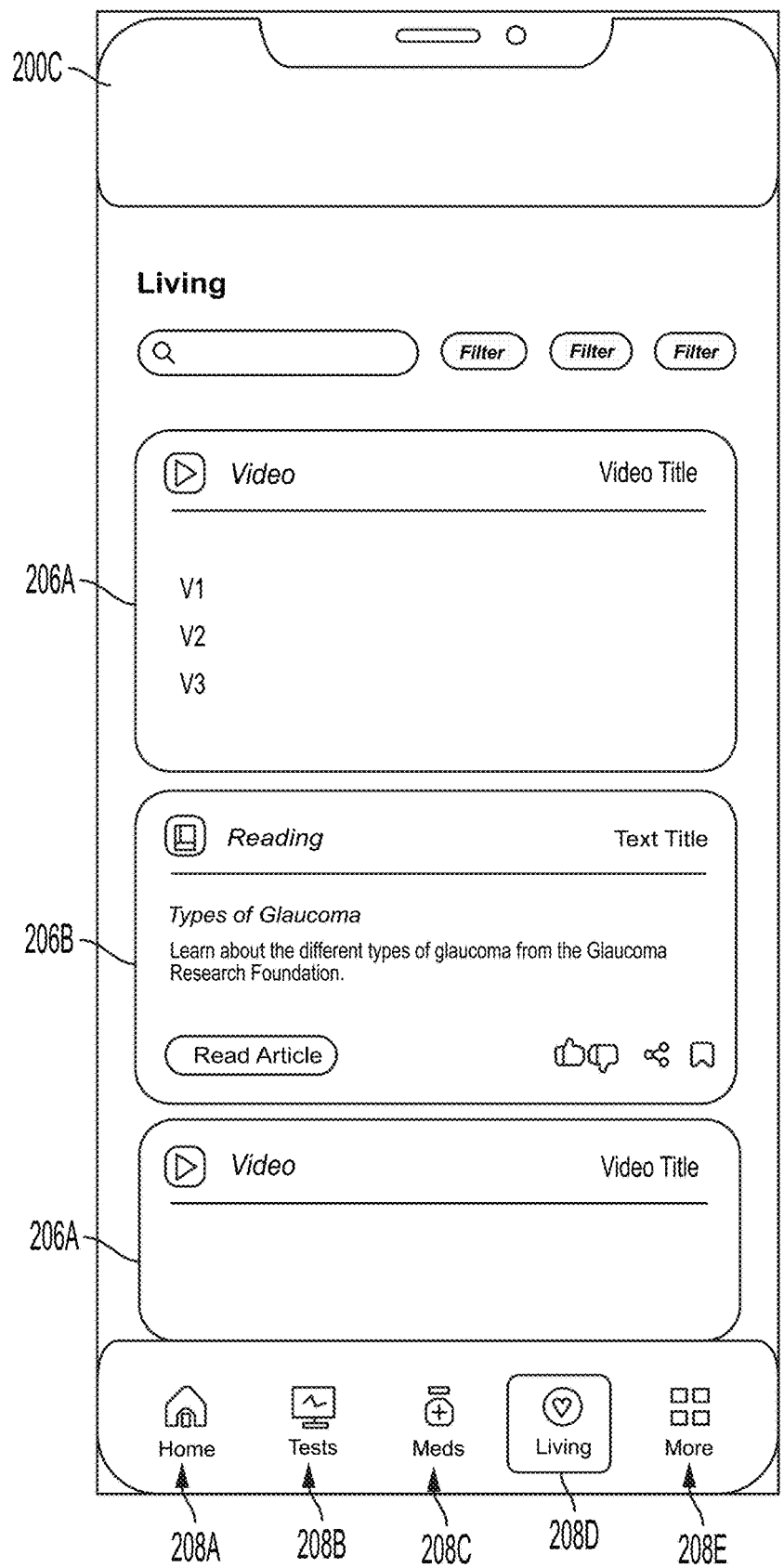

FIG. 2C is a schematic diagram of example interface 200C indicative of the living page of interface element 208D. The example interface 200C may include interface elements 206A-206B. The interface element 206A may display a listing of videos V1-V3 relevant to educating the patient about their treatment. The interface element 206B may display a listing of references relevant to educating the patient about their treatment. Some of the content displayed by example interface 200C may be based on personalized recommendations driven by machine learning.

Figure 2D:
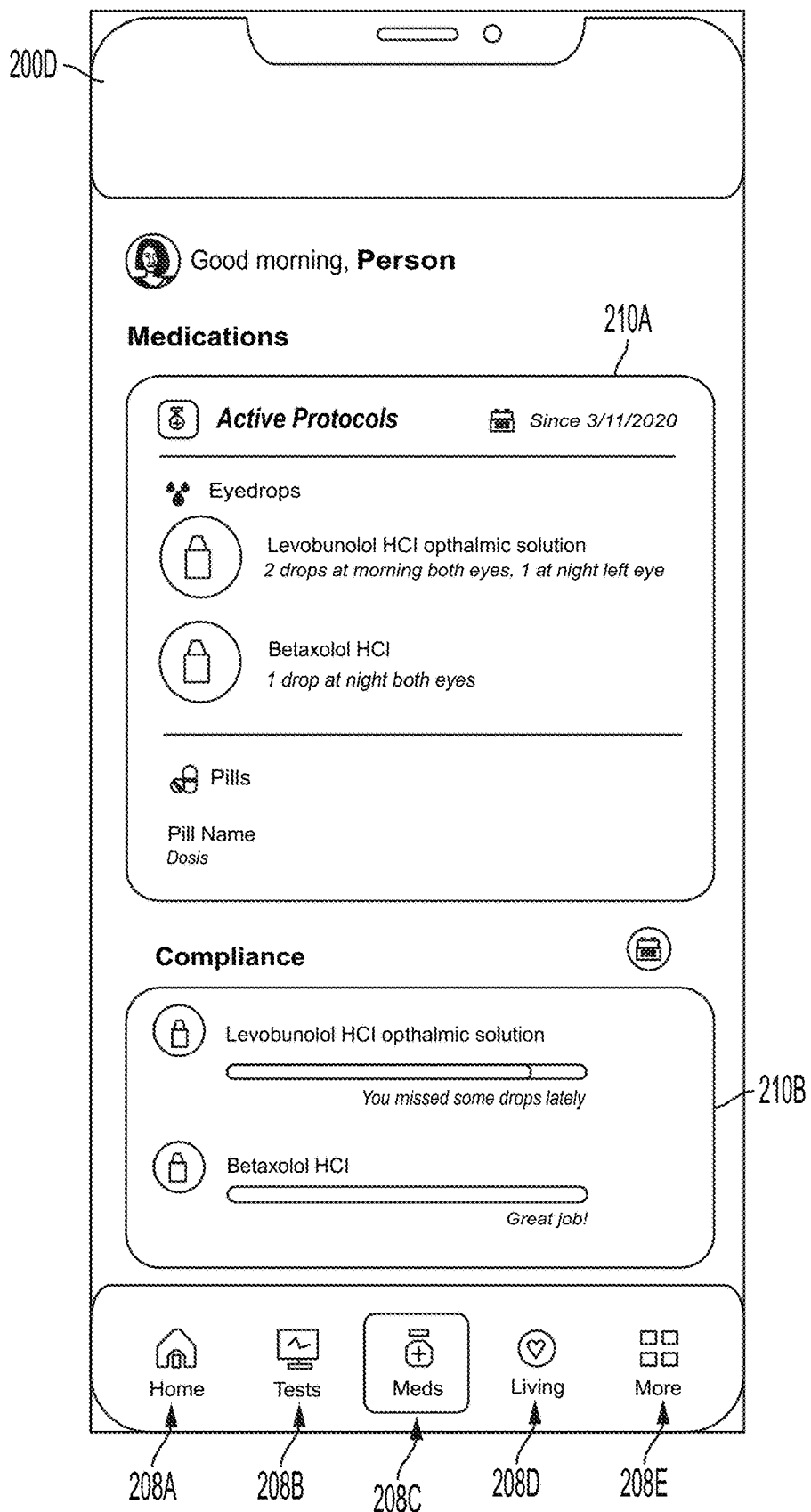

FIG. 2D is a schematic diagram of example interface 200D indicative of the medication page of interface element 208C. The example interface 200D may include interface elements 210A-210B. The interface element 210A may display a listing of the medications prescribed to the patient. The interface element 210B may display the patient's compliance to taking their medications as requested. The remote monitoring service may track the patient's compliance to determine if their treatment is progressing.

In this case, the remote monitoring service may operate on a mobile device. However, the remote monitoring service may operate on any portable system, such as a tablet or the like. Moreover, the remote monitoring system may operate on remote computer system.

Figure 3:
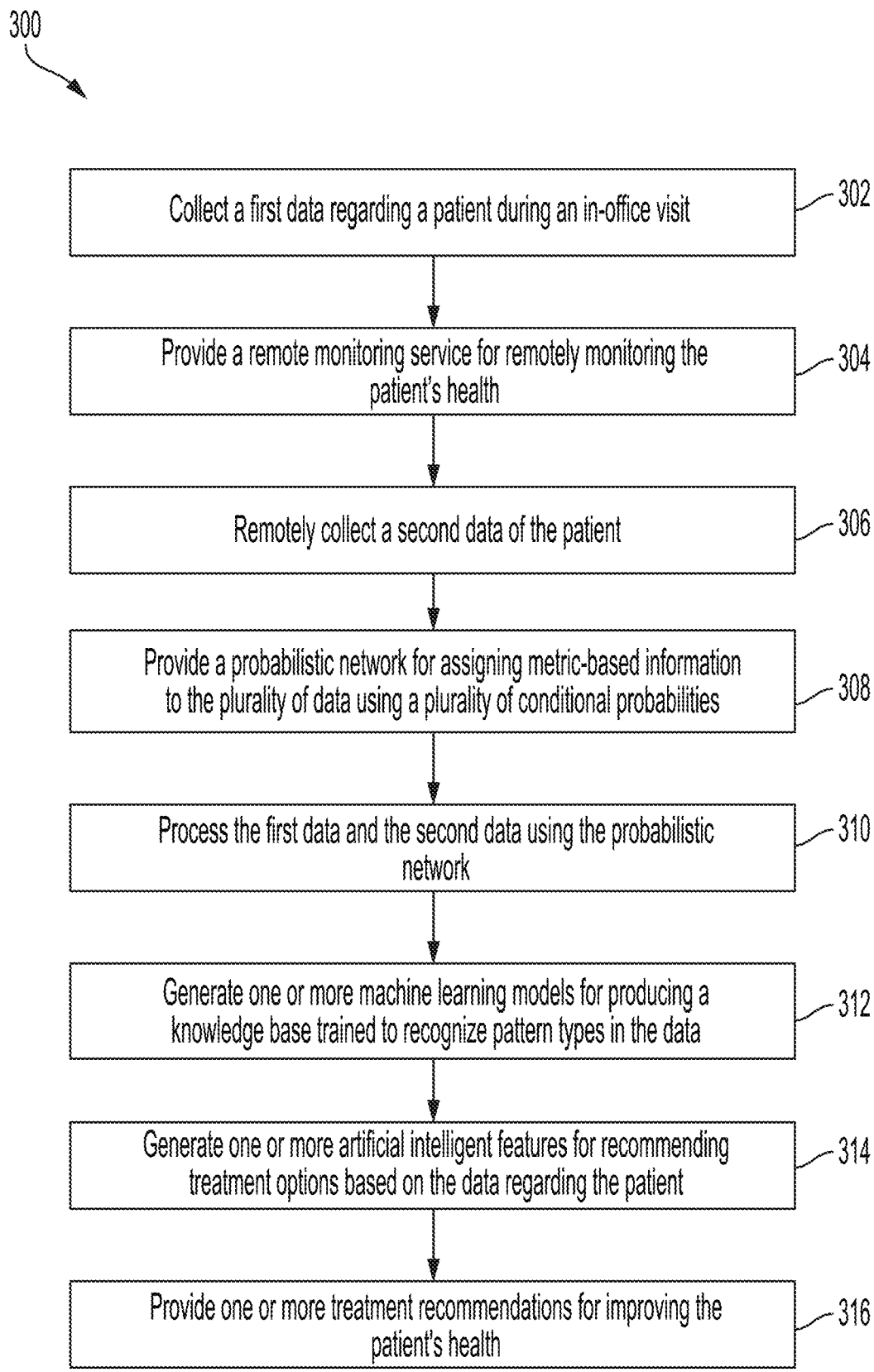
FIG. 3 is a workflow illustrating a method for monitoring health, in accordance with some embodiments.

FIG. 3 is a workflow 300 illustrating a method for monitoring health, in accordance with some embodiments. At block 302, the method includes collecting, using at least one processor, a first data regarding a patient during an in-office visit. At block 304, the method includes providing, using the at least one processor, a remote monitoring service for remotely monitoring the patient's health. At block 306, the method includes remotely collecting, using the remote monitoring service and the at least one processor, a second data of the patient. At block 308, the method includes providing, using the at least one processor, a probabilistic network for assigning metric-based information to the first data and the second data using a plurality of conditional probabilities.

At block 310, the method includes processing, using the at least one processor and the probabilistic network, the first data and the second data using the probabilistic network. At block 312, the method includes generating, using the at least one processor and the processed plurality of data, one or more machine learning models for producing a knowledge base trained to recognize pattern types in the data. At block 314, the method includes generating, using the at least one processor and the knowledge base, one or more artificial intelligent features for recommending treatment options based on the data regarding the patient. At block 316, the method includes providing, using the at least one processor and the one or more artificial intelligent features, one or more treatment recommendations for improving the patient's health.

Figure 4:
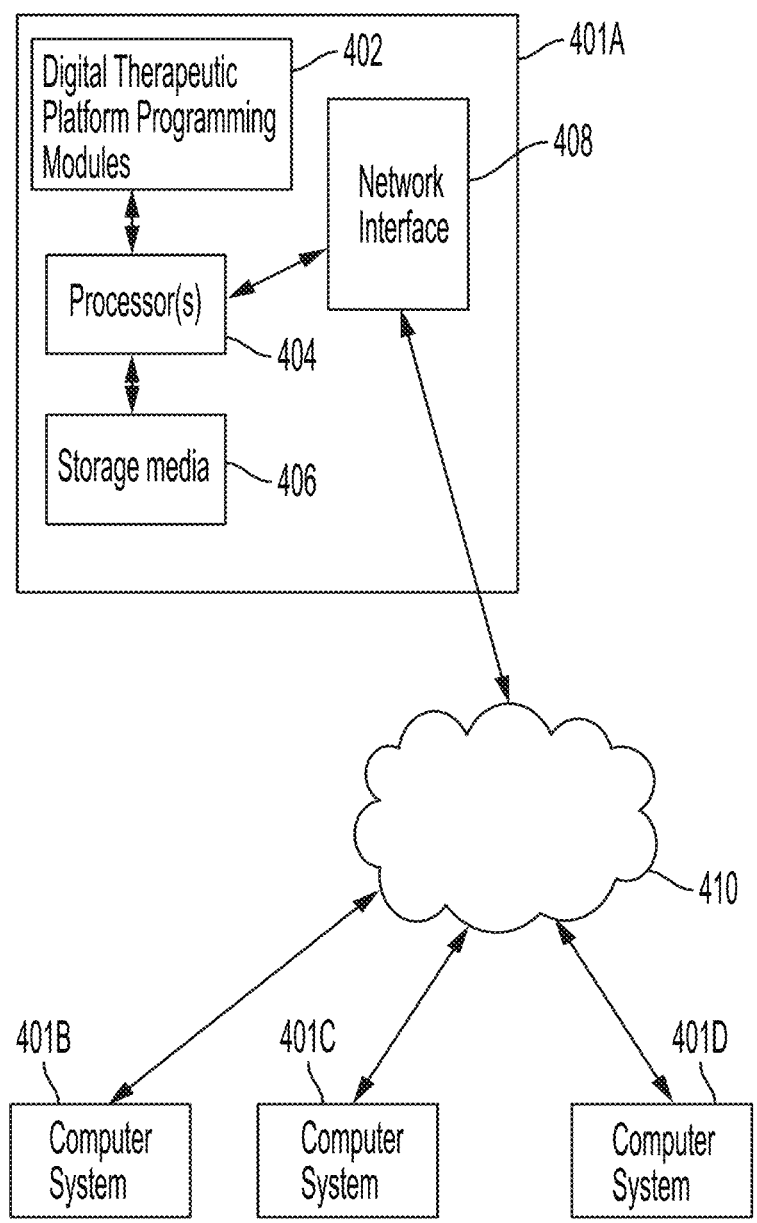
FIG. 4 is a schematic diagram of an example computing system carrying out some of the methods of the present disclosure, in accordance with some embodiments.

FIG. 4 depicts an example computing system 400 carrying out some of the methods of the present disclosure, in accordance with some embodiments. For example, the computing system 400 may perform the workflow 300, techniques, and methodologies described herein.

The computing system 400 can be an individual computer system 401A or an arrangement of distributed computer systems. The computer system 401A includes one or more digital therapeutic platform modules 402 that are configured to perform the various tasks of the digital therapeutic platform described herein according to some embodiments. To perform these various tasks, digital therapeutic platform modules module 402 executes independently, or in coordination with, one or more processors 404, which is (or are) connected to one or more storage media 406. The processor(s) 404 is (or are) also connected to a network interface 408 to allow the computer system 401A to communicate over a data network 410 with one or more additional computer systems and/or computing systems, such as 401B, 401C, and/or 401D (note that computer systems 401B, 401C and/or 401D may or may not share the same architecture as computer system 401A, and may be located in different physical locations. Note that data network 410 may be a private network, it may use portions of public networks, it may include remote storage and/or applications processing capabilities (e.g., cloud computing).

A processor can include a microprocessor, microcontroller, processor module or subsystem, programmable integrated circuit, programmable gate array, or another control or computing device.

The storage media 406 can be implemented as one or more computer-readable or machine-readable storage media. Note that while in the example embodiment of FIG. 4 storage media 406 is depicted as within computer system 401A, in some embodiments, storage media 406 may be distributed within and/or across multiple internal and/or external enclosures of computing system 401A and/or additional computing systems. Storage media 406 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs), BluRays or any other type of optical media; or other types of storage devices. "Non-transitory" computer readable medium refers to the medium itself (i.e., tangible, not a signal) and not data storage persistency (e.g., RAM vs. ROM).

Note that the instructions or methods discussed above can be provided on one or more computer-readable or machine-readable storage medium, or alternatively, can be provided on multiple computer-readable or machine-readable storage media distributed in a large system having possibly plural nodes and/or non-transitory storage means. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions or located at a remote site from which machine-readable instructions can be downloaded over a network for execution.

It should be appreciated that computer system 401A is one example of a computing system, and that computer system 401A may have more or fewer components than shown, may combine additional components not depicted in the example embodiment of FIG. 4, and/or computer system 401A may have a different configuration or arrangement of the components depicted in FIG. 4. The various components shown in FIG. 4 may be implemented in hardware, software, or a combination of both, hardware and software, including one or more signal processing and/or application specific integrated circuits.

It should also be appreciated that while no user input/output peripherals are illustrated with respect to computer systems 401A, 401B, 401C, and 401D, many embodiments of computing system 400 include computing systems with keyboards, touch screens, displays, etc. Some computing systems in use in computing system 400 may be desktop workstations, laptops, tablet computers, smartphones, server computers, etc.

Further, the steps in the processing methods described herein may be implemented by running one or more functional modules in an information processing apparatus such as general-purpose processors or application specific chips, such as ASICs, FPGAs, PLDs, or other appropriate devices. These modules, combinations of these modules, and/or their combination with general hardware are included within the scope of protection of the disclosure.

In some embodiments, a computing system is provided that comprises at least one processor, at least one memory, and one or more programs stored in the at least one memory, wherein the programs comprise instructions, which when executed by the at least one processor, are configured to perform any method disclosed herein.

In some embodiments, a computer readable storage medium is provided, which has stored therein one or more programs, the one or more programs comprising instructions, which when executed by a processor, cause the processor to perform any method disclosed herein.

In some embodiments, a computing system is provided that comprises at least one processor, at least one memory, and one or more programs stored in the at least one memory; and means for performing any method disclosed herein.

In some embodiments, an information processing apparatus for use in a computing system is provided, and that includes means for performing any method disclosed herein.

In some embodiments, a graphics processing unit is provided, and that includes means for performing any method disclosed herein.

Reference in the specification to "one implementation" or "an implementation" means that a particular feature, structure, or characteristic described in connection with the implementation is included in at least one implementation of the disclosure. The appearances of the phrase "in one implementation," "in some implementations," "in one instance," "in some instances," "in one case," "in some cases," "in one embodiment," or "in some embodiments" in various places in the specification are not necessarily all referring to the same implementation or embodiment.

The digital therapeutic platform described herein may provide an ongoing diagnostic and therapeutic advantage to the patient for the specific treatment of certain eye ailments, such as glaucoma or the like, and associated potential behavioral and cognitive associations. By providing a patient's treating physician(s) with an ongoing digital diagnostic and prescriptive product, potentially enhanced outcomes may be achieved when compared to medical treatment alone. The prescriptive digital advantage may provide a personalized model for patients where medical treatment options (drugs and surgery) can be refined incorporating consistent home-based diagnostic testing, suggesting alterations in the therapeutic process without office visits, while cognitive overlay may be monitored as supportive to the patient's mental health needs.

Finally, the above descriptions of the implementations of the present disclosure have been presented for the purposes of illustration and description. It is not intended to be exhaustive or to limit the present disclosure to the precise form disclosed. Many modifications and variations are possible in light of the above teaching. It is intended that the scope of the present disclosure be limited not by this detailed description, but rather by the claims of this application. As will be understood by those familiar with the art, the present disclosure may be embodied in other specific forms without departing from the spirit or essential characteristics thereof. Accordingly, the present disclosure is intended to be illustrative, but not limiting, of the scope of the present disclosure, which is set forth in the following claims.

What is claimed is:

1. A method for determining whether an update to one or more machine learning models is needed, the method comprising:

receiving, using at least one processor, a plurality of data regarding a patient, wherein the plurality of data comprises first input data, and wherein the first input data comprises first historic patient data;

initiating, using the at least one processor, a probabilistic network comprising a plurality of conditional probabilities;

weighting, using at least one processor and the probabilistic network, the plurality of data, wherein the weighting of the plurality of data comprises the probabilistic network assigning metric-based information to the plurality of data;

processing, using the at least one processor, the plurality of data using the probabilistic network, wherein the processing of the plurality of data comprises combining at least a first data and a second data comprised within the plurality of data;

generating, using the at least one processor and a processed plurality of data, one or more machine learning models for producing a knowledge base trained to recognize patterns in at least one of the plurality of data or the processed plurality of data, the one or more machine learning models comprising:

a feature learning component, wherein the feature learning component allows for the knowledge base to recognize data patterns;

data sets used for modeling, wherein the data sets comprise training data;

a model builder, wherein the model builder comprises a file or group of files trained to recognize data patterns related to defined pathologies using the data sets; and an evaluator, wherein the evaluator determines if an update to the one or more machine learning models created by the model builder is needed;

generating, using the at least one processor and the knowledge base, one or more features for recommending treatment options based on the knowledge base;

generating, using the at least one processor and the one or more features, one or more treatment recommendations, wherein the at least one processor and the one or more features generates the one or more treatment recommendations at least in part by using the file or the group of files comprised in the model builder and the knowledge base;

transmitting, using the at least one processor, the one or more treatment recommendations;

receiving, using at least one processor, second input data, wherein the second input data is captured by a first computing device, wherein the first computing device is communicatively coupled to a remote server, and wherein the second input data comprises remote monitored diagnostic data; and updating, using the at least one processor and the evaluator, the knowledge base, wherein the knowledge base is updated according to a determination by the evaluator that an update to the one or more machine learning models created by the model builder based on the received second input data is needed.

2. The method of claim 1, wherein the plurality of data further comprises medical data of the patient collected during an in-office visit.

3. The method of claim 1, wherein the plurality of data comprises medical data of the patient collected during a virtual office visit.

4. The method of claim 1, wherein the probabilistic network comprises a belief-based network of conditional probabilities.

5. The method of claim 4, wherein the conditional probabilities are Bayesian or Bayes conditional probabilities.

6. The method of claim 1, further comprising:
aggregating, using one or more machine learning algorithms, the plurality of data;
generating, using the one or more machine learning algorithms, at least one data pattern associated with the plurality of data; and
training, using the machine learning algorithms, the knowledge base to recognize the at least one data pattern associated with the plurality of data, wherein the at least one data pattern associated with the plurality of data is used to generate the one or more features.

7. The method of claim 1, further comprising classifying, using the at least one processor, the plurality of data.

8. The method of claim 7, wherein the at least one processor classifies the plurality of data using one or more of a random decision forest, a linear classifier, support vector machine, recurrent neural network, feedforward neural network, radial basis function network, self-organizing map, learning vector quantization, Hopfield network, Boltzmann machine, echo state network, long or short term memory, bi-directional recurrent neural network, hierarchical recurrent neural network, stochastic neural network, modular neural network, associative neural network, deep neural network, deep belief network, convolutional neural network, convolutional deep belief network, large memory storage and retrieval neural network, deep Boltzmann machine, deep stacking network, tensor deep stacking network, spike and slab restricted Boltzmann machine, compound hierarchical-deep model, deep coding network, multilayer kernel machine, or deep Q-network.

9. A method for determining whether an update to one or more machine learning models is needed, the method comprising:
receiving, using at least one processor, a first data regarding a patient during an in-office visit, wherein the first data comprises first historic patient data;
initiating, using the at least one processor, a remote monitoring service;
receiving, from the remote monitoring service and using the at least one processor, a second data of the patient;
initiating, using the at least one processor, a probabilistic network comprising a plurality of conditional probabilities;
weighting, using at least one processor and the probabilistic network, the first data and the second data, wherein the weighting of the first data and the second data comprises the probabilistic network assigning metric-based information to the first data and the second data;
processing, using the at least one processor and the probabilistic network, the first data and the second data, wherein the processing of the first data and the second data comprises combining at least a third data comprised in the first data and a fourth data comprised in the second data, and wherein the result is a processed plurality of data;
generating, using the at least one processor and the processed plurality of data, one or more machine learning models for producing a knowledge base trained to recognize patterns in at least one of the first data or the second data or the processed plurality of data, the one or more machine learning models comprising:
a feature learning component, wherein the feature learning component allows for the knowledge base to recognize data patterns;
data sets used for modeling, wherein the data sets comprise training data;
a model builder, wherein the model builder comprises a file or group of files trained to recognize data patterns related to defined pathologies using the data sets; and
an evaluator, wherein the evaluator determines if an update to the one or more machine learning models created by the model builder is needed;
generating, using the at least one processor and the knowledge base, one or more features for recommending treatment options based on the knowledge base;
generating, using the at least one processor and the one or more features, one or more treatment recommendations, wherein the at least one processor and the one or more features generates the one or more treatment recommendations at least in part by using the file or the group of files comprised in the model builder and the knowledge base;
transmitting, using the at least one processor, the one or more treatment recommendations;
receiving, using at least one processor, fifth data, wherein the fifth data is captured by a first computing device, wherein the first computing device is communicatively coupled to a remote server, and wherein the fifth data comprises remote monitored diagnostic data; and
updating, using the at least one processor and the evaluator, the knowledge base, wherein the knowledge base is updated according to a determination by the evaluator that an update to the one or more machine learning models created by the model builder based on the received fifth data is needed.

10. The method of claim 9, wherein the second data further comprises test results of at least one test taken by the patient remotely.

11. The method of claim 9, wherein the fifth data further comprises test results of at least one test taken by the patient remotely.

12. The method of claim 9, wherein the second data and the fifth data originate from the same source.

13. The method of claim 9, wherein the remote monitoring service further comprises the first computing device, wherein the first computing device is communicatively coupled to a remote server.

14. The method of claim 9, wherein the remote monitoring service further comprises a second computing device, wherein the second computing device is communicatively coupled to at least one of the first computing device or the remote server.

15. The method of claim 9, further comprising:
aggregating, using one or more machine learning algorithms, the first data and the second data;
generating, using the one or more machine learning algorithms, at least one data pattern associated with the aggregated first and second data; and
training, using the machine learning algorithms, the knowledge base to recognize the at least one data pattern associated with the aggregated first and second data, wherein the at least one data pattern associated with the aggregated first and second data is used to generate the one or more features.

16. The method of claim 9, wherein generating the one or more treatment recommendations comprises analyzing at least one data pattern identified by the one or more machine learning models in the first data, the second data, and the fifth data.

17. The method of claim 9, wherein generating the one or more treatment recommendations comprises analyzing at least one data pattern identified by the one or more machine learning models in the processed plurality of data.

18. The method of claim 9, wherein the processed plurality of data comprises the fifth data.

19. A system for determining whether an update to one or more machine learning models is needed, the system comprising:
one or more computing device processors; and
one or more computing device memories, coupled to the one or more computing device processors, the one or more computing device memories storing instructions executed by the one or more computing device processors, wherein the instructions are configured to:
receive a first data regarding a patient, wherein the first data comprises first historic patient data;
initiate a remote monitoring service;
receive, from the remote monitoring service, a second data of the patient;
initiate a probabilistic network comprising a plurality of conditional probabilities;
weight, using the probabilistic network, the first data and the second data, wherein the weighting of the first data and the second data comprises the probabilistic network assigning metric-based information to the first data and the second data;
process the first data and the second data using the probabilistic network, the first data and the second data, wherein the processing of the first data and the second data comprises combining at least a third data comprised in the first data and a fourth data comprised in the second data, and wherein the result is a processed plurality of data;
generate, using the processed plurality of data, one or more machine learning models for producing a knowledge base trained to recognize patterns in at least one of the first data or the second data or the processed plurality of data, the one or more machine learning models comprising:
a feature learning component, wherein the feature learning component allows for the knowledge base to recognize data patterns;
data sets used for modeling, wherein the data sets comprise training data;
a model builder, wherein the model builder comprises a file or group of files trained to recognize data patterns related to defined pathologies using the data sets; and
an evaluator, wherein the evaluator determines if an update to the one or more machine learning models created by the model builder is needed;
generate, using the knowledge base, one or more features for recommending treatment options based on the knowledge base;
generate, using the one or more features, one or more treatment recommendations, wherein the one or more features generates the one or more treatment recommendations at least in part by using the file or the group of files comprised in the model builder and the knowledge base;
transmit the one or more treatment recommendations;
receive fifth data, wherein the fifth data is captured by a first computing device, wherein the first computing device is communicatively coupled to a remote server, and wherein the fifth data comprises remote monitored diagnostic data; and
update the knowledge base, wherein the knowledge base is updated according to a determination by the evaluator that an update to the one or more machine learning models created by the model builder based on the received fifth data is needed.

20. The system of claim 19, wherein the fifth data further comprises test results of at least one test taken by the patient remotely, wherein the at least one test comprises at least one of an OCT scan, visual fields test, visual acuity test, optic nerve imaging, or an eye pressure test.

* * * * *